US012642617B2

(12) United States Patent (10) Patent No.: US 12,642,617 B2
Egle (45) Date of Patent: Jun. 2, 2026

(54) MEDICAL DEVICE WITH MEDICAL DEVICE HINGE

(71) Applicant: Karl Storz SE & Co. KG, Tuttlingen (DE)

(72) Inventor: Michael Egle, Böttingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 321 days.

(21) Appl. No.: 16/211,789

(22) Filed: Dec. 6, 2018

(65) Prior Publication Data

US 2019/0175297 A1      Jun. 13, 2019

(30) Foreign Application Priority Data

Dec. 13, 2017      (DE) ..................... 10 2017 129 692.1

(51) Int. Cl.
| | |
|---|---|
| *A61B 50/20* | (2016.01) |
| *A61B 1/00* | (2006.01) |
| *A61B 90/50* | (2016.01) |
| *A61B 90/57* | (2016.01) |
| *F16C 11/00* | (2006.01) |
| *E05D 5/00* | (2006.01) |
| *F16C 11/04* | (2006.01) |

(52) U.S. Cl.
CPC .......... *A61B 50/20* (2016.02); *A61B 1/00149* (2013.01); *A61B 90/50* (2016.02); *A61B 90/57* (2016.02); *F16C 11/00* (2013.01); *E05D 5/00* (2013.01); *F16C 11/04* (2013.01)

(58) Field of Classification Search
CPC ........... A61B 50/20; A61B 5/20; A61B 90/57;
A61B 9/50; A61B 90/20; Y10T
403/32918; Y10T 403/3296; Y10T
403/32943; F16C 11/045; F16C 11/04;
F16C 11/00
See application file for complete search history.

(56) References Cited

U.S. PATENT DOCUMENTS

| | | | | |
|---|---|---|---|---|
| 3,522,962 A | * | 8/1970 | Poker, Jr. .............. | F16C 11/045 |
| | | | | 277/366 |
| 4,435,100 A | * | 3/1984 | Cox ....................... | F16C 11/045 |
| | | | | 411/383 |
| 4,491,436 A | * | 1/1985 | Easton .................. | F16C 11/045 |
| | | | | 403/122 |

(Continued)

FOREIGN PATENT DOCUMENTS

DE      10 2013 002 498 A1      8/2013

*Primary Examiner* — Jennifer Pitrak McDonald
*Assistant Examiner* — Jennifer L Ghand
(74) *Attorney, Agent, or Firm* — McGlew and Tuttle, P.C.

(57) ABSTRACT

A medical device has a first hinge part (17) including two hinge arms (15, 16), which are arranged at a distance apart, and a hinge pin (32; 52), which is extended between the hinge arms along a longitudinal axis (38; 55). A second hinge part (18) is in certain areas accommodated between the two hinge arms and is passed through by a hinge cavity (31; 51). The hinge pin is accommodated in a pivotably movably in the hinge cavity. The hinge pin and the hinge cavity have a central contact region (33; 56) with contact between hinge pin and hinge cavity. Clearance regions (36, 37; 57, 58) border the contact region on both sides and are extended up to the hinge arms, without touching contact between hinge pin and hinge cavity, in order to ensure an exclusively central force transmission between the hinge pin and the hinge cavity.

19 Claims, 2 Drawing Sheets

(56) References Cited

U.S. PATENT DOCUMENTS

| | | | | |
|---|---|---|---|---|
| 2005/0057800 A1* | 3/2005 | Obrebski | ............... | G02B 7/001 |
| | | | | 359/385 |
| 2007/0027469 A1* | 2/2007 | Smith | .............. | A61B 17/07207 |
| | | | | 606/205 |
| 2007/0138992 A1* | 6/2007 | Prisco | .................... | A61B 34/30 |
| | | | | 318/568.21 |
| 2011/0138574 A1* | 6/2011 | Bogue | .................... | B64D 29/06 |
| | | | | 29/402.09 |
| 2013/0144395 A1* | 6/2013 | Stefanchik | ............. | A61B 17/29 |
| | | | | 623/20.11 |
| 2014/0046345 A1* | 2/2014 | Armenteros | ......... | A61B 17/122 |
| | | | | 606/139 |

* cited by examiner

MEDICAL DEVICE WITH MEDICAL DEVICE HINGE

CROSS REFERENCE TO RELATED APPLICATIONS

This application claims the benefit of priority under 35 U.S.C. § 119 of German Application 10 2017 129 692.1, filed Dec. 13, 2017, the entire contents of which are incorporated herein by reference.

TECHNICAL FIELD

The invention relates to a medical device comprising a hinge arrangement which is configured for a pivot motion of a first hinge part in relation to a second hinge part, having a first hinge part, which comprises two hinge arms, which are arranged at a distance apart, and a hinge pin, which is extended between the hinge arms along a longitudinal axis and defines a pivot axis of the hinge arrangement, and having a second hinge part, which in certain areas is accommodated between the two hinge arms and which is passed through by a hinge cavity, wherein the hinge pin is accommodated in a pivotably movable manner in the hinge cavity.

BACKGROUND

A hinge arrangement of this type is used, for instance, in a holder for a medical instrument, wherein it can be provided to fix the medical instrument with a clamping device, said clamping device comprising a hinge arrangement.

SUMMARY

An object of the invention consists in providing a hinge arrangement which, even in the event of an occasional application of high forces, ensures a low friction for a pivot motion of the two hinge parts relative to each other.

It is herein provided that the hinge pin and the hinge cavity has a central contact region, with a touching contact between hinge pin and hinge cavity, and clearance regions, which border the contact region on both sides and are extended up to the hinge arms, without touching contact between hinge pin and hinge cavity, in order to ensure an exclusively central force transmission between the hinge pin and the hinge cavity.

The exclusively central force transmission means that the hinge pin, away from the contact region in the two clearance regions, when forces are applied to the two hinge parts, can perform a deflection motion and can hereupon be elastically deformed. Undesirable friction effects between the hinge pin and the hinge cavity, which in the long term could lead to damaging of the hinge arrangement, can hence be avoided. When a force and/or a torque is applied to the two hinge parts, the hinge pin, away from the contact region in the respective clearance region, is deformed in an S-shape. Insofar as a force is applied to the two hinge parts exclusively in a direction transversely to the longitudinal axis, the hinge pin is deformed in an S-shape in mirror symmetry to a mirror plane which is oriented perpendicular to the longitudinal axis. If, on the other hand, a torque is applied to the two hinge parts, wherein the torque about a torque axis oriented transversely to the longitudinal axis, then an S-shaped deformation of the hinge pin in the respective clearance regions takes place in axial symmetry to the torque axis.

It is expedient if the hinge cavity is configured as a stepped bore having a centrally arranged guide bore which has a smaller cross section than clearance bores which border this same on both sides. A cost-effective creation of the guide bore is thereby enabled, since only the clearance bores must have a larger cross section, while the guide bore has a smaller cross section, the profiling of which is matched in such a way to a profiling of the hinge pin that the hinge pin can form with the guide bore a slide bearing. Preferredly, it is provided that the guide bore and the clearance bores are respectively of circular cylindrical configuration and, in particular, are arranged coaxially to one another. In addition, it can be provided that the cross sections of the two clearance bores are identical.

Preferably, it is provided that the hinge pin between the hinge arms is configured with a constant profiling. Preferably, the hinge pin has a circular profiling and is thus designed as a circular cylinder, whereby a cost-effective manufacturing method for the hinge pin can be realized.

In an alternative refinement of the invention, it is provided that the hinge pin is configured with a centrally arranged guide portion, which has a larger cross section than clearance portions which border this same on both sides. As a result, a particularly advantageous elasticity for the hinge pin can be realized, since the centrally arranged guide portion, due to its larger cross section, within the framework of the maximum forces envisioned for the hinge arrangement, can be formed dimensionally stable, while the clearance portions which border this same, due to the smaller cross section, can be elastically deformed already in case of forces markedly below the maximum forces envisioned for the hinge arrangement. Preferably, both the guide portion and the clearance portions which border this same are respectively of circular cylindrical configuration and arranged coaxially to one another.

In a further embodiment of the invention, it is provided that the hinge cavity is configured as a bore having a constant profiling. The hinge cavity can hence be created by a single production procedure, in particular a drilling procedure.

It is advantageous if the hinge pin is configured with a centrally arranged guide portion, which has a larger cross section than clearance portions which border this same on both sides, and that the hinge cavity is configured as a stepped bore having a centrally arranged guide bore, which has a smaller cross section than clearance bores which border this same on both sides. Through the matching of the cross sections of the clearance portions to the cross sections of the clearance bores, an advantageous adjustment of the desired elasticity for the hinge arrangement can be obtained.

Preferredly, it is provided that mutually opposing surfaces of the hinge arms form with adjacent surfaces of the second hinge part a sliding guide with play, and that the hinge pin and the hinge cavity are mutually coordinated in such a way that, when the second hinge part is tilted in relation to the first hinge part about a tilt axis oriented transversely to the longitudinal axis, an exclusively elastic deformation of the hinge pin obtains. The sliding guide between the two hinge parts serves, in particular, to absorb forces or force components which are oriented parallel to the longitudinal axis of the hinge pin and are not supported by the hinge pin and the corresponding hinge cavity. In addition, the sliding guide between the two hinge parts serves to limit a tilting between the first hinge part and the second hinge part about a tilt axis oriented transversely to the longitudinal axis. Due to the elasticity of the hinge pin, in comparison to known hinge arrangements which are realized with rigid hinge pins, larger tilt angles for the two hinge parts relative to one another can be accepted. As a result, a clamp mounting, for instance, which is equipped with a hinge arrangement according to the invention can favorably adapt to different external geometries of objects to be clamped without an undesirable stiffness of the hinge arrangement having to be accepted in return.

It is expedient if an extent of the central contact region in the direction of the longitudinal axis amounts to less than 30 percent, preferably less than 25 percent, of an extent of one of the clearance regions in the direction of the longitudinal axis.

In an advantageous refinement of the invention, it is provided that a cross-sectional area of the guide bore amounts to less than 50 percent, preferably less than 40 percent, in particular less than 30 percent, of a cross-sectional area of the clearance bore.

In a further embodiment of the invention, it is provided that a cross-sectional area of the clearance portion amounts to less than 50 percent, preferably less than 40 percent, in particular less than 30 percent, of a cross-sectional area of the guide portion.

Advantageous embodiments of the invention are represented in the drawing. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 2:
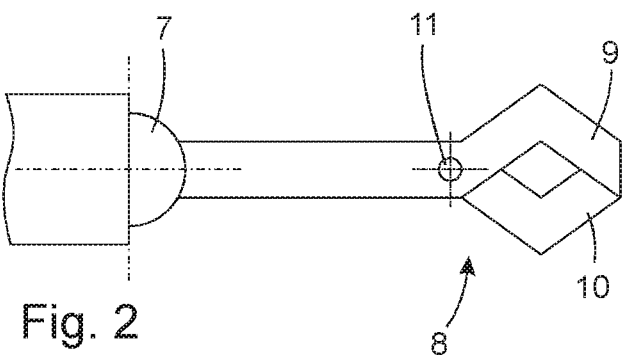
FIG. 2 is a schematic detailed representation of the clamping device according to FIG. 1.
Figure 1:
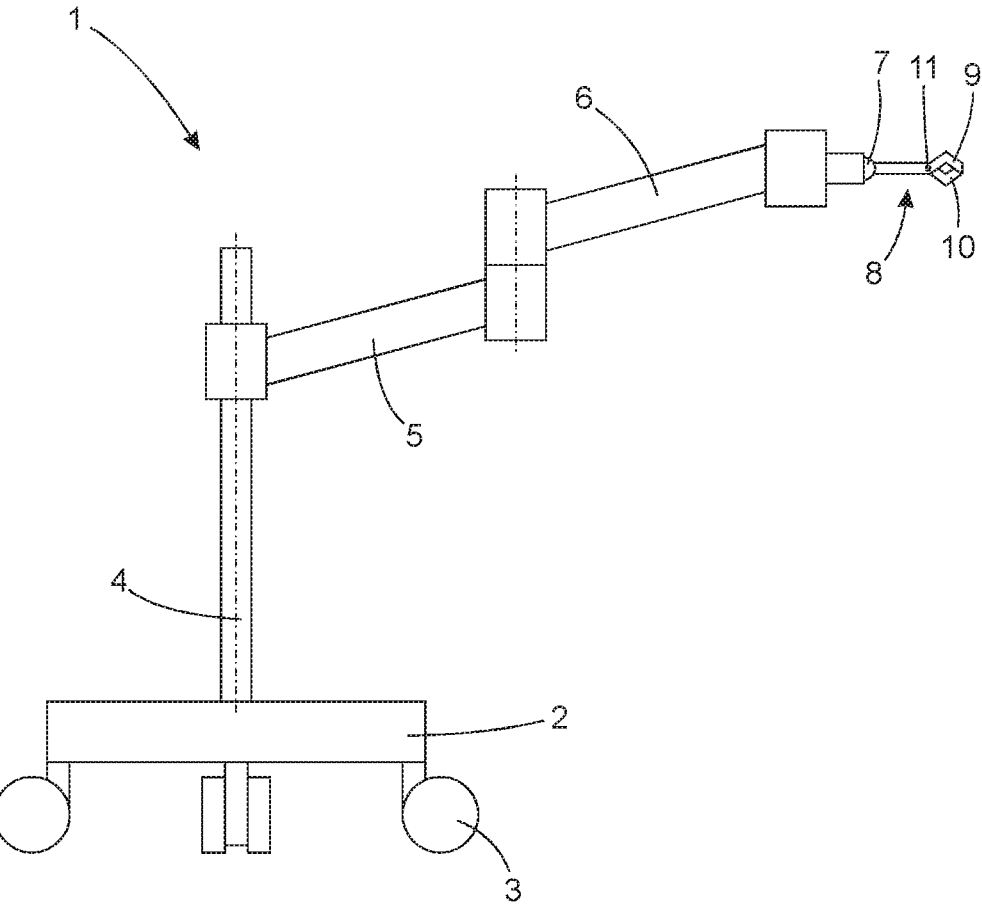
FIG. 1 is a schematic representation of a medical device which comprises a hinge arrangement as a component part of a clamping device.

Referring to the drawings, a medical device 1 represented in FIG. 1 is configured, purely by way of example, as a mobile supporting arm for a medical instrument (not represented in detail), for instance an endoscopic camera systems.

The medical device 1 comprises a base frame 2, which is equipped with rollers 3 and which has a column 4 which extends upward substantially in the vertical direction. On the column 4, a first supporting arm portion 5 is arranged such that it is adjustable in height and is pivotable about a vertical axis, which first supporting arm portion, on an end region facing away from the column 4, is coupled with a second supporting arm portion 6 which, for its part, is mounted such that it is pivotably movable on the first supporting arm portion 5 about a vertical axis (not represented).

On that end region of the second supporting arm portion 6 which is facing away from the first supporting arm portion 5 is configured, purely by way of example, with the interposition of a ball joint 7, a gripping arrangement 8, which comprises a fixed gripper claw 9 and a movable gripper claw 10. The fixed gripper claw 9 and the movable gripper claw 10 here form a hinge arrangement 11, which enables the pivotably movable relative movement of the movable gripper claw 10 in relation to the fixed gripper claw 9.

Figure 3:
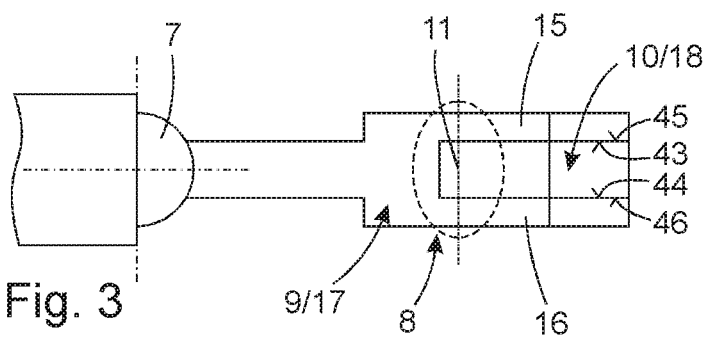
FIG. 3 is a schematic top view of the clamping device according to FIG. 2.

As can be seen from the schematic representation of FIG. 3, the fixed gripper claw 9, on an end region facing away from the ball joint 7, is of fork-shaped configuration and comprises two mutually spaced hinge arms 15, 16, between which, purely by way of example, is accommodated the movable gripper claw 10. The fixed gripper claw 9 thus forms with its hinge arms 15, 16 a first hinge part 17, while the movable gripper claw 10 forms a second hinge part 18. The two hinge parts 17, 18 are connected to each other in a pivotably movable manner by means of a hinge pin, wherein in FIGS. 4 and 5 different embodiments of hinge arrangements are represented.

Purely by way of example, in FIG. 3 the mutually facing surfaces 43, 44 of the two hinge arms 15, 16 and the mutually opposite surfaces 45, 46 of the second hinge part 18 are arranged such that no bearing play for the slide bearing is evident, which bearing play is formed by these surfaces 43 to 46 for the two hinge parts 17, 18. In practice, the respectively opposing surfaces 43 and 45 or 44 and 46 respectively have a slight distance apart so as not to jeopardize a smoothness of running for the hinge arrangement 11. Accordingly, the second hinge part 18, upon application of a torque which is oriented perpendicular to the plane of representation of FIG. 3, can induce a tilting of the second hinge part 18 in relation to the first hinge part 17, as is represented symbolically in FIG. 7.

Figures 4, 5:
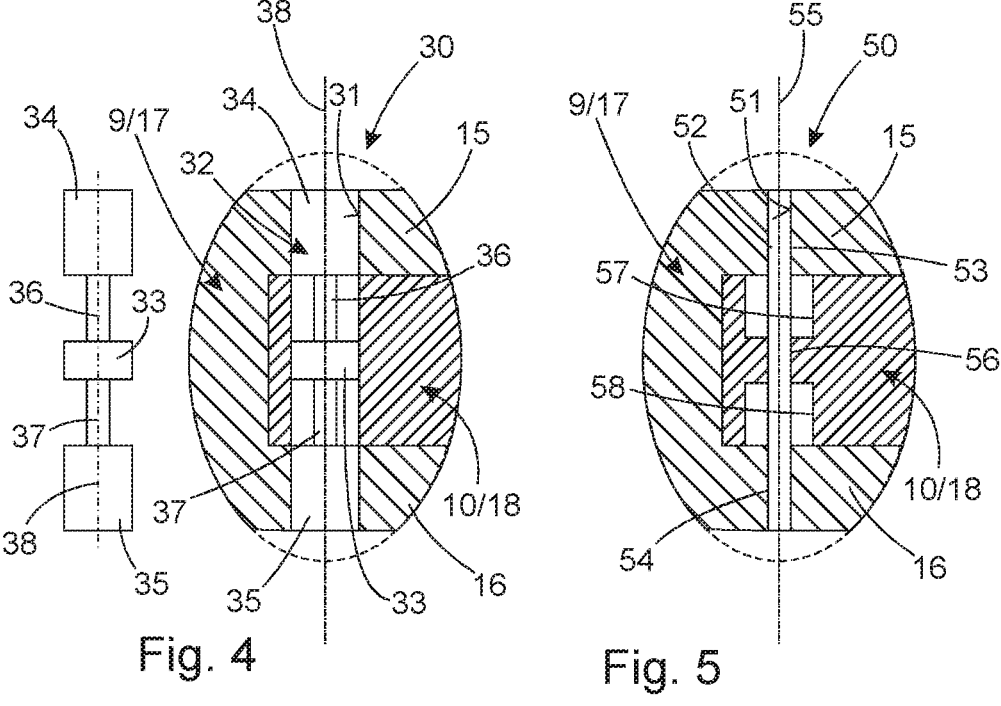
FIG. 4 is a detailed representation of the clamping device according to FIGS. 2 and 3 having a first embodiment of a hinge arrangement, in which the hinge pin is configured with a centrally arranged guide portion which has a larger cross section than clearance portions which border this same on both sides.
FIG. 5 is a detailed representation of the clamping device according to FIGS. 2 and 3 having a second embodiment of a hinge arrangement, in which the hinge cavity is configured as a stepped bore and the hinge pin has a constant profiling.

In the first embodiment of a hinge arrangement 30, which is represented in FIG. 4, the two hinge arms 15 and 16 of the first hinge part 17, as well as the second hinge part 18, are passed through by a through bore 31, which, purely by way of example, is of circular cylindrical configuration and which, with regard to the second hinge part 18, can also be referred to as a hinge cavity. In the through bore 31 is provided a hinge pin 32, which, for the illustration of its geometry additionally to the sectional representation of FIG. 4, is represented as a single part, and which is accommodated, for instance, in a frictionally engaged manner in the two hinge arms 15 and 16 and forms with the second hinge part 18 a pivot bearing. For this purpose, the hinge pin 32 comprises a centrally arranged guide portion 33, which is matched to a, preferably circular, profile of the through bore 31 in such a way that a slidingly movable relative movement between the guide portion 33 and the second hinge part 18 provided with the through bore 31 is enabled. At each end, the hinge pin 32 is provided with holding portions 34, 35, which are fixed in non-positive engagement in the hinge arms 15, 16 and hence ensure a rotationally secure connection between the hinge pin 32 and the first hinge part 17.

On both sides of the guide portion 33, along a longitudinal axis 38 serving as a pivot axis for the second hinge part 18, clearance portions 36, 37 respectively extend up to the holding portions 34 or 35. The clearance portions 36 and 37 here have a considerably smaller cross section, in particular a considerably smaller diameter, than the guide portion 33. Through this geometric design of the hinge pin 32, it is ensured that a force transmission between the second hinge part 18 and the hinge pin 32 fixed to the first hinge part 17 obtains exclusively in the region of the guide portion 33, and that the clearance portions 36 and 37, due to their, compared with the guide portion 33, considerably smaller cross sections, enable an advantageous elasticity for the hinge arrangement 33.

In the second embodiment (represented in FIG. 5) of a hinge arrangement 50, in which the hinge pin 52 is accommodated in non-positive engagement in guide portions 53, 54 of the hinge arms 15, 16 and has along a longitudinal axis 55 a constant profiling, the hinge cavity configured as a through bore 51 is realized as a stepped bore. The through bore 51 herein comprises a centrally arranged guide bore 56, the cross section of which is matched to the cross section of the hinge pin 52 so as to form a pivotably movable slide bearing. Away from the guide bore 56 extend clearance bores 57, 58, which border this same on both sides and secure the clearance regions without touching contact between the hinge pin 52 and the through bore 51 that serves as the hinge cavity.

Figures 6, 7:
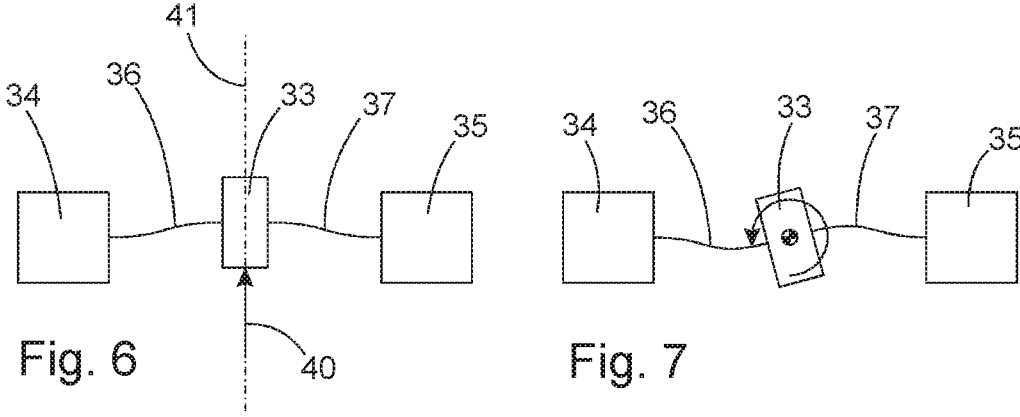
FIG. 6 is a schematized representation of a hinge pin upon an exclusive application of radial forces.
FIG. 7 is a schematized representation of a hinge pins upon an exclusive application of a torque about a torque axis oriented transversely to a longitudinal axis of the hinge pin.

From the purely schematic representation of FIGS. 6 and 7, which relate to the hinge pin 32 according to the first embodiment of the hinge arrangement 30, yet also apply in similar fashion to the hinge arrangement 50, it emerges that, upon application of a purely radial force 40, which, via the second hinge part 18, is mounted in the guide portion 33, an S-shaped deformation of the two clearance portions 36, 37 is realized in mirror symmetry to a mirror plane 41.

When a torque 42 is applied to the guide portion 33 about a torque axis oriented perpendicular to the plane of representation of FIG. 7, there is obtained, on the other hand, a tilting of the guide portion 33 in relation to the holding portions 34 and 35, in which the clearance portions 36 and 37 are likewise respectively deformed in an S-shape, wherein the geometric relationship between the two clearance portions 36 and 37 is here a mirroring about the torque axis.

While specific embodiments of the invention have been shown and described in detail to illustrate the application of the principles of the invention, it will be understood that the invention may be embodied otherwise without departing from such principles.

The invention claimed is:

1. A medical device comprising a hinge arrangement, the hinge arrangement comprising:
   a first hinge part comprising a first hinge part interior surface, a first hinge arm and a second hinge arm, the first hinge arm and the second hinge arm being arranged spaced apart by a distance;
   a second hinge part accommodated in certain areas between the first hinge arm and the second hinge arm and configured for a pivot motion of the first hinge part about a pivot axis in relation to the second hinge part, the second hinge part having a hinge cavity surface defining a hinge cavity that passes through the second hinge part, the first hinge part interior surface defining at least a portion of a second hinge part interior space for receiving at least a portion of the second hinge part, the first hinge part interior surface being in contact with the portion of the second hinge part, the first hinge part interior surface extending continuously from a position adjacent to a portion of one of the two hinge arms to another position adjacent to a portion of another one of the two hinge arms, the first hinge part interior surface being parallel to the pivot axis; and
   a hinge pin extending between the hinge arms along a longitudinal axis to define a pivot axis of the hinge arrangement, wherein:
   the hinge pin is elastically deformable;
   the hinge pin is pivotably movable in the hinge cavity; and
   the hinge pin has a central contact region in direct contact with the hinge cavity surface of the second hinge part;
   the hinge pin has a first clearance region without touching contact between the hinge pin and the hinge cavity surface of the second hinge part, the first clearance region extending within the second hinge part from the central contact region to the first hinge arm;
   the hinge pin has a second clearance region without touching contact between the hinge pin and the hinge cavity surface of the second hinge part, the second clearance region extending within the second hinge part between the central contact region and the second hinge arm; and
   the central contact region, the first clearance region and the second clearance region ensure an exclusively central force transmission between the hinge pin and the second hinge part.

2. A medical device according to claim 1, wherein the hinge cavity surface is configured as a stepped bore comprising:
   a centrally arranged guide bore defining the central contact region;
   a first clearance bore at a first side of the guide bore, the guide bore having a smaller cross section than the first clearance bore; and
   a second clearance bore at a second side of the guide bore, the guide bore having a smaller cross section than the second clearance bore.

3. A medical device according to claim 2, wherein the hinge pin between the first hinge arm and the second hinge arm is configured with a constant profiling.

4. A medical device according to claim 2, wherein a cross-sectional area of the guide bore amounts to less than 50 percent of a cross-sectional area of at least one of the first clearance bore and the second clearance bore.

5. A medical device according to claim 1, wherein the hinge pin comprises:
   a centrally arranged guide portion;
   a first clearance portion at a first side of the guide portion, the guide portion having a larger cross section than the first clearance portion; and
   a second clearance portion at a second side of the guide portion, the guide portion having a larger cross section than the second clearance portion.

6. A medical device according to claim 5, wherein the hinge cavity is configured as a bore having a constant profiling.

7. A medical device according to claim 5, wherein a cross-sectional area of at least one of the first clearance portion and the second clearance portion amounts to less than 50 percent of a cross-sectional area of the guide portion.

8. A medical device according to claim 1, wherein an extent of the central contact region in a direction of the longitudinal axis amounts to less than 30 percent of at least one of the first clearance region and the second clearance region, the hinge cavity surface defining at least a portion of at least one of the first clearance region and the second clearance region, the portion of the second hinge part comprising a second hinge part portion surface located between the first hinge arm and the second hinge arm, the first hinge part interior surface being in contact with an entire length of the second hinge part portion surface.

9. A medical device comprising a hinge arrangement, the hinge arrangement comprising:

a first hinge part comprising two hinge arms, which are arranged at a distance apart, and a first hinge part comprising a first hinge part interior surface;

a second hinge part, the hinge arrangement being configured for a pivot motion of the first hinge part about a pivot axis in relation to the second hinge part, the first hinge part interior surface defining at least a portion of a second hinge part interior space for receiving at least a portion of the second hinge part, the first hinge part interior surface being in contact with the portion of the second hinge part, the first hinge part interior surface extending continuously from a position adjacent to a portion of one of the two hinge arms to another position adjacent to a portion of another one of the two hinge arms, the first hinge part interior surface being parallel to the pivot axis; and an elastically deformable hinge pin extending between the hinge arms along a longitudinal axis to define a pivot axis of the hinge arrangement, wherein:

the second hinge part is, in certain areas, accommodated between the two hinge arms and the second hinge part has a hinge cavity passing through the second hinge part and wherein the hinge pin is pivotably movable in the hinge cavity; and the hinge pin has a central contact region in direct contact with the second hinge part at the hinge cavity, and the hinge pin has clearance regions, which border the contact region on both sides of the contact region and are extended within the second hinge part from the contact region up to the hinge arms, without touching contact between hinge pin and the second hinge part at the hinge cavity, in order to ensure an exclusively central force transmission between the hinge pin and the second hinge part at the hinge cavity.

10. A medical device according to claim 9, wherein the hinge cavity is configured as a stepped bore having a centrally arranged guide bore which has a smaller cross section than clearance bores which border the guide bore on both sides of the guide bore, the portion of the second hinge part comprising a second hinge part portion surface located between the two hinge arms, the first hinge part interior surface being in contact with an entire length of the second hinge part portion surface.

11. A medical device according to claim 10, wherein the hinge pin between the hinge arms is configured with a constant profiling.

12. A medical device according to claim 11, wherein a cross-sectional area of the guide bore amounts to less than 50 percent of a cross-sectional area of the clearance bore.

13. A medical device according to claim 10, wherein a cross-sectional area of the guide bore amounts to less than 50 percent of a cross-sectional area of the clearance bore.

14. A medical device according to claim 9, wherein the hinge pin is configured with a centrally arranged guide portion, which has a larger cross section than clearance portions which border this same on both sides.

15. A medical device according to claim 14, wherein the hinge cavity is configured as a bore having a constant profiling.

16. A medical device according to claim 15, wherein a cross-sectional area of the clearance portion amounts to less than 50 percent of a cross-sectional area of the guide portion.

17. A medical device according to claim 14, wherein a cross-sectional area of the clearance portion amounts to less than 50 percent of a cross-sectional area of the guide portion.

18. A medical device according to claim 9, wherein:

the hinge pin is configured with a centrally arranged guide portion, which has a larger cross section than clearance portions which border the guide portion on both sides of the guide portion, and the hinge cavity is configured as a stepped bore having a centrally arranged guide bore which guide bore has a smaller cross section than clearance bores which border the guide bore on both sides of the guide bore.

19. A medical device according to claim 9, wherein an extent of the central contact region in a direction of the longitudinal axis amounts to less than 30 percent of an extent of one of the clearance regions in the direction of the longitudinal axis.

* * * * *